United States Patent
Sablone

(10) Patent No.: US 9,434,143 B2
(45) Date of Patent: Sep. 6, 2016

(54) EXTENSIBLE LAMINAR MATERIAL, PARTICULARLY FOR SANITARY ARTICLES, AND METHOD OF PRODUCING SAME

(75) Inventor: Gabriele Sablone, Montesilvano (IT)

(73) Assignee: FAMECCANICA.DATA S.P.A., Sambuceto di San Giovanni Teatino (IT)

( * ) Notice: Subject to any disclaimer, the term of this patent is extended or adjusted under 35 U.S.C. 154(b) by 1350 days.

(21) Appl. No.: 12/989,905

(22) PCT Filed: Apr. 24, 2009

(86) PCT No.: PCT/IB2009/051691
§ 371 (c)(1),
(2), (4) Date: Oct. 27, 2010

(87) PCT Pub. No.: WO2009/133508
PCT Pub. Date: Nov. 5, 2009

(65) Prior Publication Data
US 2011/0040273 A1    Feb. 17, 2011

(30) Foreign Application Priority Data
Apr. 30, 2008  (IT) .............................. TO2008A0325

(51) Int. Cl.
*B32B 5/02* (2006.01)
*B32B 37/12* (2006.01)
(Continued)

(52) U.S. Cl.
CPC ..... *B32B 37/1292* (2013.01); *A61F 13/15593* (2013.01); *A61F 13/15739* (2013.01);
(Continued)

(58) Field of Classification Search
CPC ............ B32B 37/1292; B32B 37/144; B29C 66/7294; B29C 66/81431; B29C 66/21; B29C 65/7855; B29C 66/346; B29C 65/5057; B29C 66/436; B29C 66/1122; B29C 65/08; B29C 66/80; A61F 13/4902; A61F 13/15739
USPC .......................... 442/182, 183, 184, 328, 329
See application file for complete search history.

(56) References Cited

U.S. PATENT DOCUMENTS 5,308,345 A      5/1994  Herrin
5,554,246 A *    9/1996  Anwyll, Jr. ................... 156/253
(Continued)

FOREIGN PATENT DOCUMENTS

WO    WO 9505140 A1 *  2/1995
WO    WO 00/37005 A2    6/2000
(Continued)

OTHER PUBLICATIONS

European Application No. 07425002.8, filed Jan. 2, 2007 (43 pages).
(Continued)

*Primary Examiner* — Elizabeth M Cole
(74) *Attorney, Agent, or Firm* — Popovich, Wiles & O'Connell, P.A.

(57) ABSTRACT

An extensible laminar material 100 includes an extensible layer 106 coupled to at least one laminar layer 102, 104. The extension of the extensible layer 106 starting from a non-extended condition determines the extension of the laminar layer(s) 102, 104 while the return of the extensible layer 106 toward the non-extended condition determines the pulling of the laminar layer(s) 102, 104 into a wrinkled condition. The extensible layer 106 and at least one laminar layer 102, 104 are connected by welding to avoid their detachment. The extensible layer 106 is anchored to at least one laminar layer 102, 104 by lines of spread adhesive 108, 108'. The welded connection is absent in correspondence of the lines of spread adhesive 108, 108'. Preferably, the material is in the form of a web 100 extensible transversally to the longitudinal extension of the web with the lines of spread adhesive 108, 108' extending along the sides of the web.

12 Claims, 4 Drawing Sheets

Figure 1:
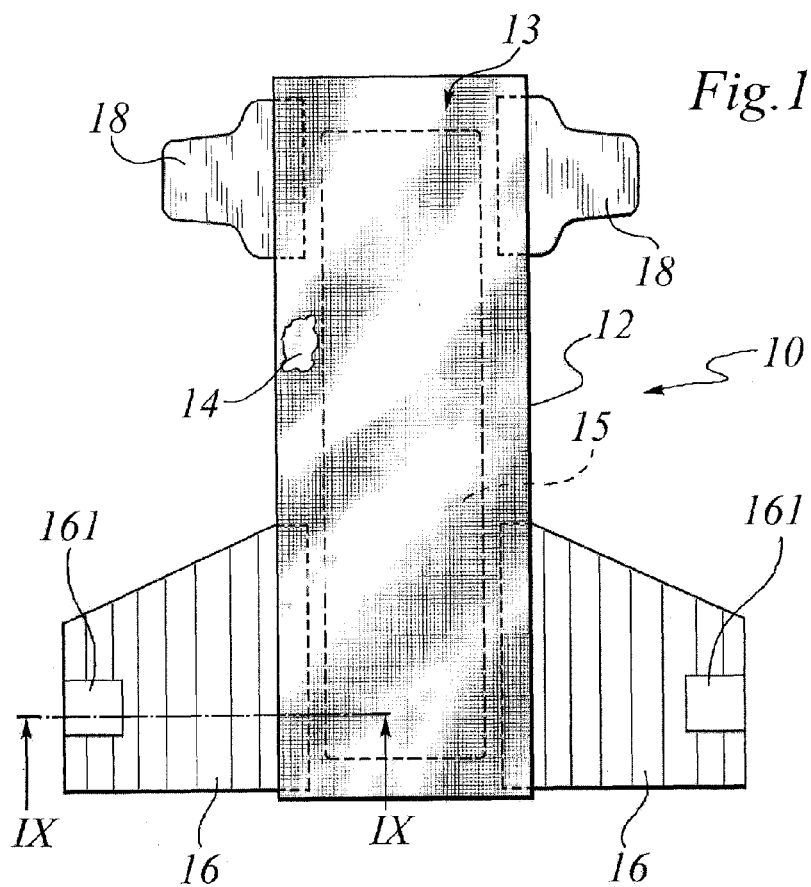

(51) Int. Cl.
*A61F 13/15* (2006.01)
*A61F 13/49* (2006.01)
*B29C 65/08* (2006.01)
*B29C 65/50* (2006.01)
*B29C 65/78* (2006.01)
*B29C 65/00* (2006.01)
*B32B 37/14* (2006.01)
*B29C 65/02* (2006.01)
*B29L 31/48* (2006.01)

(52) U.S. Cl.
CPC ..... *A61F13/15756* (2013.01); *A61F 13/4902* (2013.01); *B29C 65/08* (2013.01); *B29C 65/5057* (2013.01); *B29C 65/7855* (2013.01); *B29C 66/1122* (2013.01); *B29C 66/21* (2013.01); *B29C 66/346* (2013.01); *B29C 66/436* (2013.01); *B29C 66/7294* (2013.01); *B29C 66/80* (2013.01); *B29C 66/81431* (2013.01); *B32B 37/144* (2013.01); *B29C 65/02* (2013.01); *B29C 65/5021* (2013.01); *B29C 65/7847* (2013.01); *B29C 66/8322* (2013.01); *B29L 2031/4878* (2013.01); *B32B 2309/10* (2013.01); *B32B 2310/028* (2013.01); *B32B 2555/02* (2013.01); *Y10T 428/24025* (2015.01)

(56) References Cited

U.S. PATENT DOCUMENTS

| 5,733,401 A | 3/1998 | Linman et al. |
| 2003/0136497 A1 | 7/2003 | Hamulski et al. |
| 2005/0249915 A1 | 11/2005 | Wood et al. |

FOREIGN PATENT DOCUMENTS

| WO | WO 01/91666 A2 | 12/2001 |
| WO | WO 01/92013 A1 | 12/2001 |
| WO | WO 2008/081237 A1 | 7/2008 |

OTHER PUBLICATIONS

Sep. 10, 2009 International Search Report and Written Opinion in PCT Application No. PCT/IB2009/051691 (14 pages).

* cited by examiner

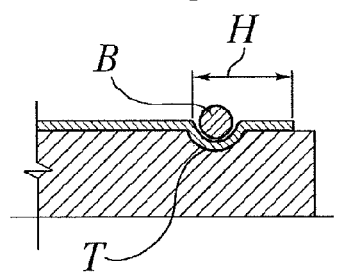
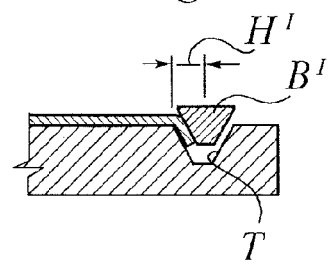
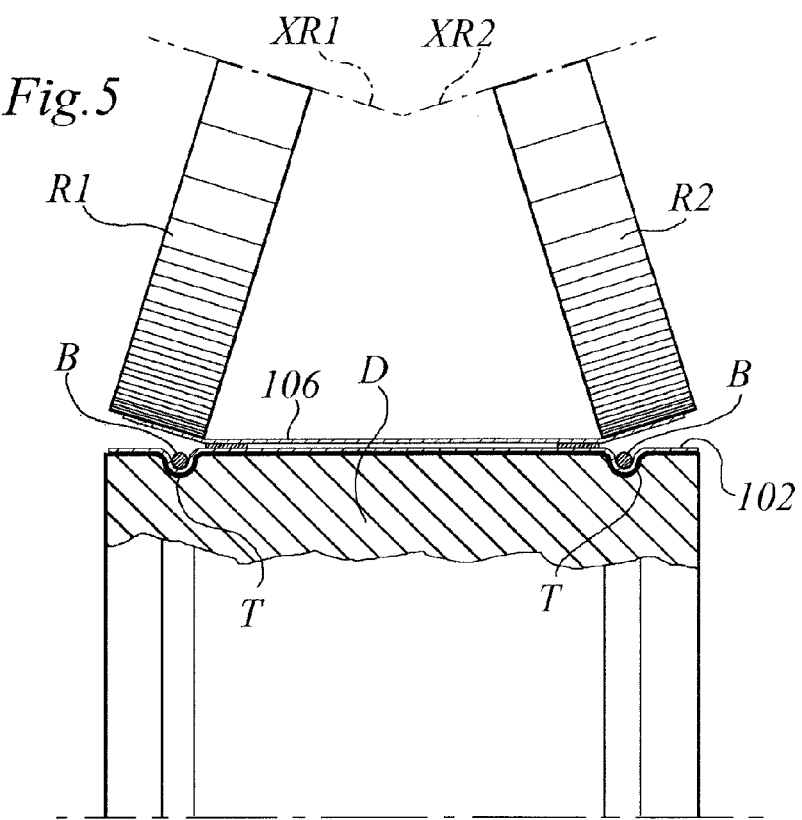
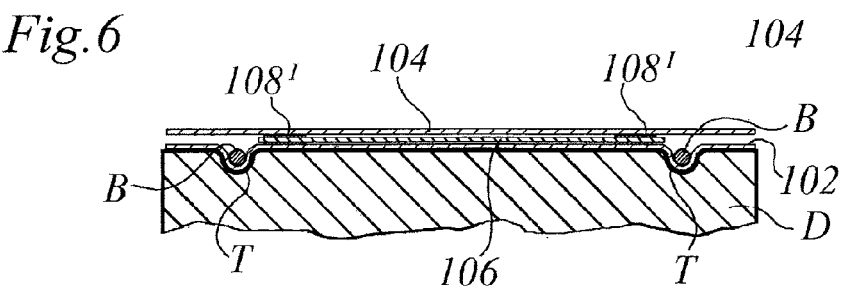

EXTENSIBLE LAMINAR MATERIAL, PARTICULARLY FOR SANITARY ARTICLES, AND METHOD OF PRODUCING SAME

FIELD OF THE INVENTION

The present description refers to extensible laminar materials.

The present description has been developed with particular reference to the possible application for the realisation of sanitary products.

DESCRIPTION OF THE RELATED ART

Documents such as WO-A-01/91666 or WO-A-01/92013 describe sanitary articles wearable as pants and comprising a central body or chassis to be arranged concave around the crotch portion of the user with side panels extending on the opposite sides of at least one of the extremities (front or rear) of the article so to be able to close the article itself around the waistline of the user.

In particular, the above-cited documents deal with the problem of realising side panels capable of combining the characteristics of elastic extensibility and breathability.

OBJECT AND SUMMARY OF THE INVENTION

The practical employment of such known solutions, although having provided totally satisfying results, have highlighted the fact that the extensible laminar material used in realising such side panels is susceptible to additional improvement, in particular concerning:

the degree of elastic extensibility of the material, and
the elastic behaviour, meaning the trend of the degree of extension as a function of the traction force applied to the material.

In various fields of application (in particular in the realisation of sanitary products wearable as pants) the need is felt for the availability of extensible laminar materials with a degree of elastic extensibility in the order of 200%, that is, the extended material having a length equal to three times the length of the material "at rest", that is, not subjected to traction solicitations.

Furthermore, particularly in the realisation of large articles such as incontinence products for adults, using extensible laminar material that, once a maximum extensibility value is reached, are further extensible only to a rather modest degree. Such characteristic is particularly appreciated for the fact that, while fitting well, that is, adapting to the morphology and tastes of the user, the article is not so slack or loose that it slides down in an undesired way.

The present invention has the object of providing an extensible laminar material capable of satisfying the above-stated needs in an excellent way.

According to the present invention, such object is achieved by means of an extensible laminar material having the characteristics specifically recalled in the claims that follow.

The invention concerns also a corresponding method of production.

The claims form an integral part of the technical disclosure provided herein relative to the invention.

BRIEF DESCRIPTION OF THE ANNEXED DRAWINGS

Figure 9:
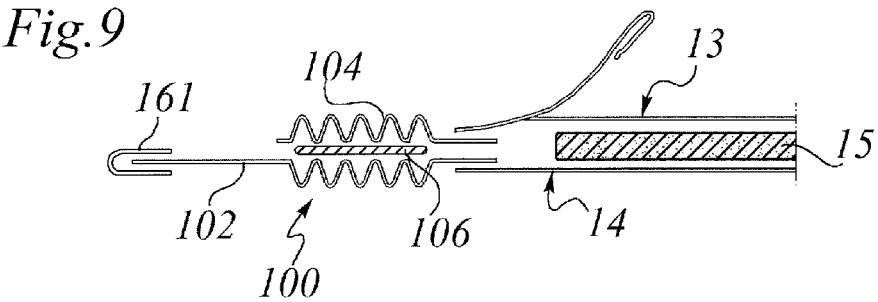
Figure 10:
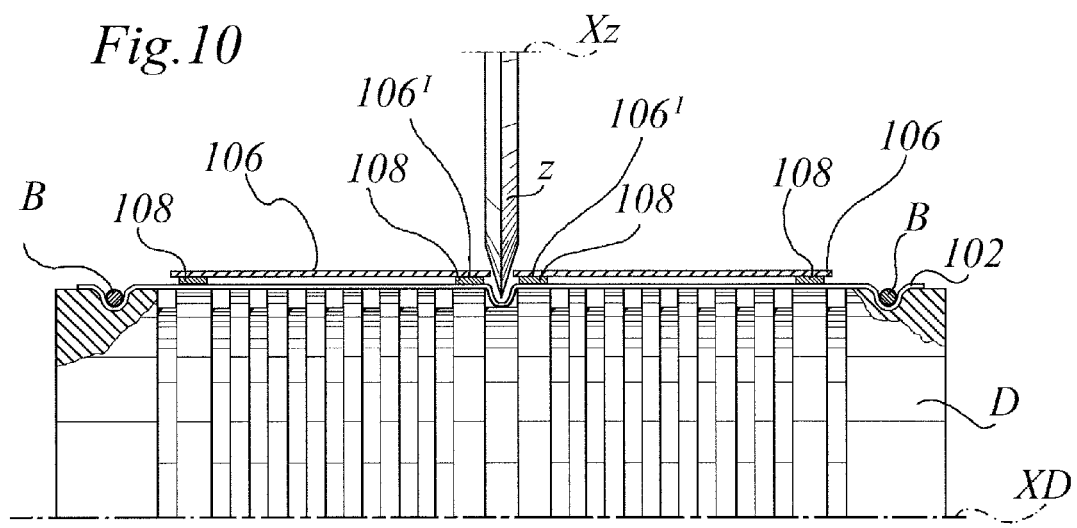

The invention will now be described by way of non-limiting example only, with reference to the annexed drawings, wherein FIG. 1 is a general schematic view of a sanitary article, illustrated in extended position, obtainable with the employment of an extensible laminar material of the type described herein, FIGS. 2 to 8 illustrate successive phases in the fabrication of such material, FIG. 9, substantially comparable to a section along the line IX-IX of FIG. 1, represents an element realised with an extensible laminar material of the type described herein, and FIG. 10 illustrates a possible variant of the method of production of the material.

DETAILED DESCRIPTION OF EMBODIMENTS

In the description that follows various specific details are illustrated aimed at a thorough understanding of the embodiments. The embodiments can be practiced without one or more of the specific details or with other methods, components, materials, etc. In other instances, known structures, materials or operations are not shown or described in detail to avoid obscuring the various aspects of the embodiments.

Reference throughout this specification to "one embodiment" or "an embodiment" means that a particular feature, structure or characteristic described in connection with the embodiment is included in at least one embodiment. Thus, the appearance of the phrases "in one embodiment" or in "an embodiment" possibly present in various places throughout this specification do not necessarily refer to the same embodiment. Furthermore, the particular features, structures or characteristics may be combined in any suitable manner in one or more embodiments.

The headings provided herein are for convenience only and thus do not interpret the field of protection or the scope of the embodiments.

In FIG. 1 the reference numeral 10 indicates a sanitary product wearable as pants in its entirety, illustrated here in a flat, extended position. In the example illustrated, it is a conventional article (baby diaper, or adult incontinence product) intended to be sold open and to be closed pants-like after being placed on the user's body. However, the solution described herein is susceptible of being applied also to the articles currently denominated "training pants" intended to be sold already closed in the pant configuration and to be pulled onto the body of the user: on this matter, see WO-A-01/91666 or WO-A-01/92013 previously cited.

The product 10 illustrated herein includes central body 12 intended to have a general U-conformation conferred thereto and be applied on the user's body, wrapping it around the crotch portion of the user.

The body or chassis 12 has a structure wherein the following are usually recognisable (in addition to various other accessory elements):

an upper layer or topsheet 13 permeable to the evacuated body liquids, intended to face toward the body of the user;

a lower layer or backsheet 14 impermeable to the body liquids, intended to face toward the outside, that is, in the opposite position with respect to the body of the user; and an absorbent mat or core 15 interposed between the topsheet 13 and the backsheet 14.

Elastic side panels are also present, indicated with the references 16, extending from the central body 12, and allowing (for example, by means of adhesive tabs 161 or micro hooks) closure of the article around the waistline as when worn by the user.

The side panels can be present at both extremities (front and rear) of the central body 12. This is usually the case in articles of the training pants type, where the distal margins of the various panels are sealed together to provide the article as it is sold, with the closed conformation. It should be pointed out that the indications "front" and "rear" are used herein only to distinguish the two extremities and therefore have no specific relevance concerning the way in which the product is eventually worn.

The embodiment illustrated herein refers to the case (more frequent in the products sold "open") wherein the side panels 16 are at the rear extremity of the central body 12, while the two wings 18 protrude laterally from the front extremity of the central body 12 providing the article 10 (ideally seen in open and extended position, such as is represented in FIG. 1) with the typical hourglass conformation.

The representation in FIG. 1 is schematic in nature and is intended to highlight the fact that the solution described herein is susceptible of being applied to a wide variety of possible types of embodiments of the article 10.

For a more detailed illustration of additional characteristics of the article 10 (for example, concerning the presence of shaped edges—usually provided on the backsheet 14 of the product—following the contour of the openings for the legs of the user and also for the presence of so-called cuffs or elastic edges arranged along the sides of the absorbent nucleus 15 functioning to contain laterally the bodily fluxes) the reader is directed to the broad existing literature on the topic; this also regarding the choice of possible materials constituting the various parts of the article 10.

The side panels 16 can be obtained starting from a tape or web of material 100, for example resorting to the solution described in detail in the European patent application 07425002.8.

The present description refers mainly to such web material and the relative production method thereof.

Generally, such material has a stratified structure constituted of two outer laminar layers 102, 104—for example of non-woven fabric—between which an elastically extensible material 106 is interposed.

For example, the layers 102 and 104 can be comprised of non-woven fabric having a specific weight in the order of 10 g/m$^2$, commercially available from the company Fibertex, under the trade name Hydrophobic NW SMS Spunbond XW 010 01 001 or FW 010 01 001. The elastic material 106 can consist of the material available from the Tredegar company, under the trade name CEX802WR.

Reference to such specific materials is by way of example only and should not be interpreted as limiting the scope of the present description.

Figure 2:
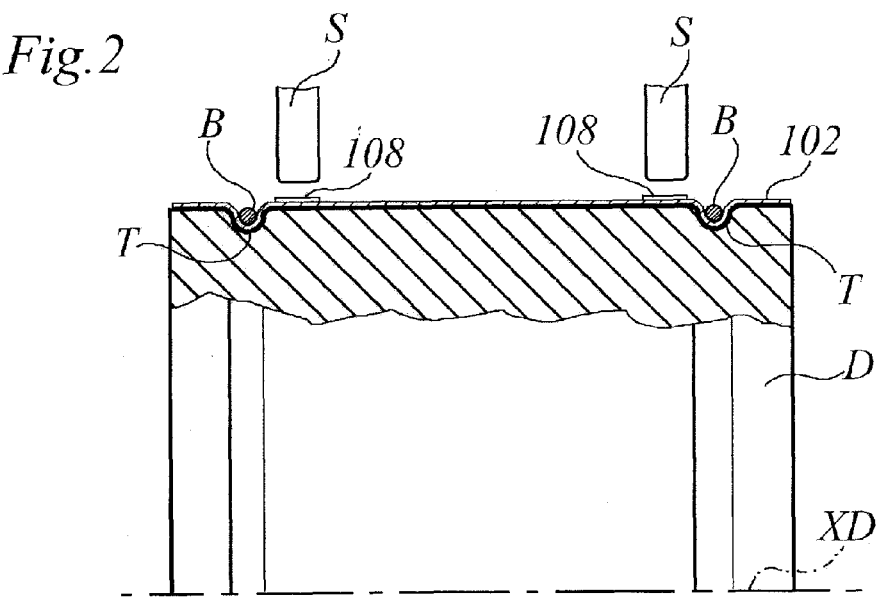

FIG. 2 of the annexed drawings illustrates a first phase of the method of production of the web material 100 wherein the layer 102 is made to advance on a roller D rotating around an axis XD while along the sides of the tape of material 102, strips (continuous or discontinuous) of adhesive material 108 are spread, by means of spreading nozzles S.

The adhesive material in question can be, for example, the glue available from the National company, under the trade name 173B.

In one embodiment, the strips 108 have a width (measured transversely with respect to the longitudinally extending direction of the web of material 100) in the order of 2-10 mm. In a currently preferred embodiment, the strips 108 have a width of 4-6 mm. In one embodiment, the lines 108 are applied with 0.1-0.2 g of glue per linear meter of spreading line (measured in the longitudinally extending direction of the web 100).

As will be appreciated more fully from reading the rest of the present description, although FIG. 2 refers to the application of two lines of spread glue 108, the solution described herein is suitable for being actuated also with a greater number of lines of spread glue.

FIG. 2 also shows that the layer 102 is retained on the roller or drum D in correspondence to its sides so that the layer 102 cannot contract transversally with respect to its longitudinally extending direction.

This result, illustrated in general terms in FIG. 2, can be obtained in different ways. For example, FIG. 3 refers in greater detail to a solution (known in itself) wherein the roller or drum D has two annular grooves T of semicircular section in which two small belts B having circular sections are wound. Always by way of example, FIG. 4 refers to another solution (itself also known) in which the roller or drum D has two annular grooves T with trapezoidal section, in which two small belts B' with complementary trapezoidal section are wound. This solution allows reduction to a minimum of the quantity of material H, H' used for the purpose of the anchoring action, and which is thus not actively used in the tape 102. The belts "pinch" the sides of the tape 102 into the grooves T, maintaining the tape 102 extended, preventing it from contracting, curling transversely.

In the next phase, represented in FIG. 5, the tape of elastic material 106 is applied to the tape 102—in extended condition: if the layer 102 were not retained in correspondence to its sides, thus resisting the pulling action of the layer 106, the tape 102 would contract, curling transversely.

As has already been said, the result of maintaining the tape 102 extended, avoiding that it contract and curl transversely, can be obtained in different ways: to cite other solutions, in addition to those illustrated, one can contemplate vacuum anchoring onto the roller D or restraint by means of counter-rollers or lateral surfaces having high friction.

The extensible layer 106 is applied over the layer 102, making it adhere to the strips of adhesive 108 in correspondence to its lateral edges.

The layer of elastic material 106 is applied to the layer 102 in extended condition (transversely with respect to the length of the web 100).

In one embodiment, the degree of extension imparted to the extensible material 106 is in the order of 200%. This means that the layer 106 is applied to the layer 102 (making it adhere to the strips 108 in correspondence to its lateral edges) maintaining it stretched transversally at a width substantially equal to three times the width that the layer 106 would have at rest (that is, in the absence of solicitation to transversal extension).

In one embodiment, the transversal extension of the tape 106 is obtained by means of a divaricating device comprising two wheels R1, R2 with corresponding axes XR1, XR2 incident and oblique to each other.

The tape of elastic material 106 is fed to the wheels R1, R2 where the peripheries of the two wheels are closer together due to their corresponding oblique rotational axes. Rotation of the wheels gradually brings the tape 106 to the zone in which the peripheries of the wheels R1, R2 are farther apart, obtaining the desired transversal elastic stretching, and then the material 106 is applied to the layer 102 in such extended condition.

A similar technique for transversal extension of laminar materials is known in the art in numerous possible variations, such as is demonstrated, for example, by the document U.S. Pat. No. 5,308,345, making a detailed description of this solution in the present application unnecessary.

The anchoring action obtained by means of the strips of adhesive material 108 ensure that the layer of material 106 maintains the extended condition even when, disengaged from the transversal extension group comprising the wheels R1 and R2. In fact, the strips 108 anchor the layer 106 laterally to the layer 102 and the sides of the layer 102 are themselves pinched into the throats T by the belts B, so that—in spite of the elastic pulling action of the layer 106—the composite tape formed by the layers 102 and 106 is maintained extended and cannot contract transversally.

At this point, as is illustrated schematically in FIG. 6, the layer 104 is applied onto the elastic layer 106 so to complete the sandwich structure of the web material 100.

Figure 7:
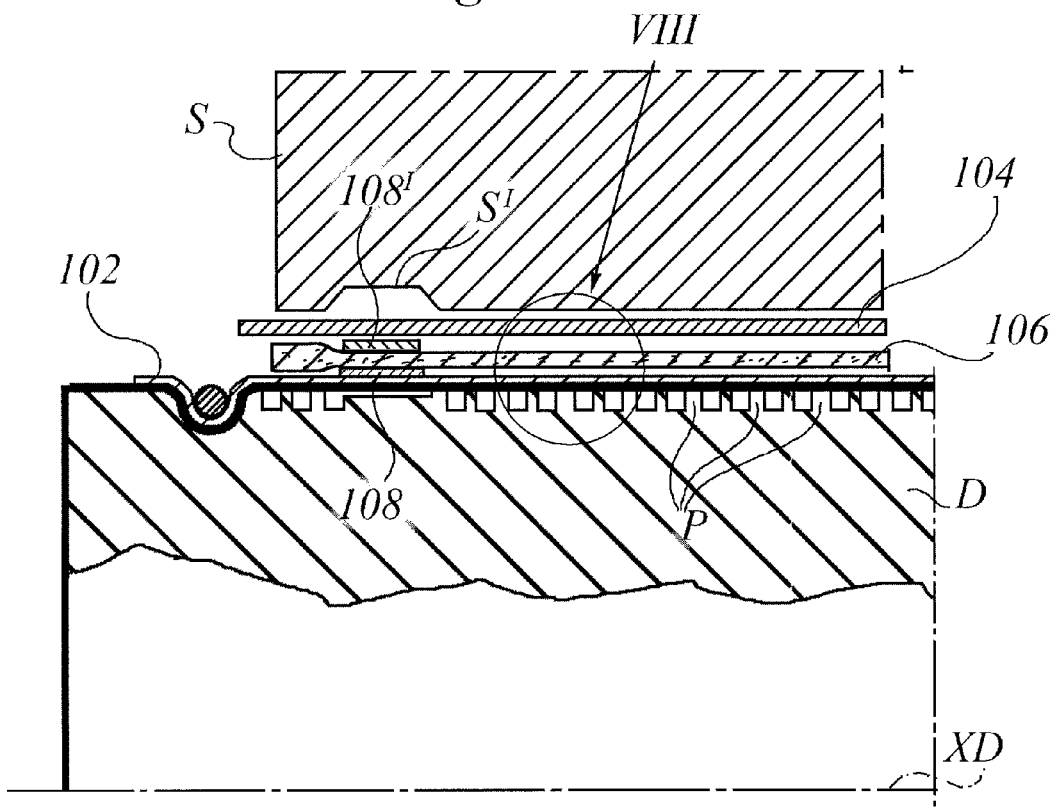
Figure 8:
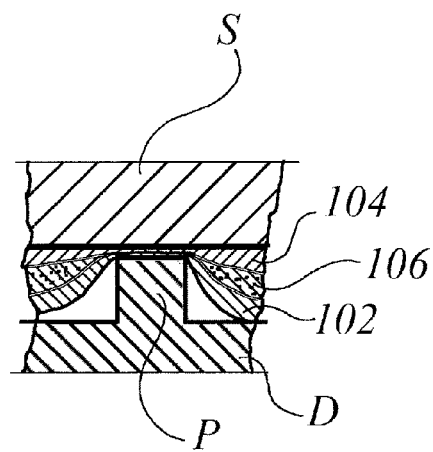

As is represented in FIGS. 7 and 8, the sandwich comprising the layers 102, 104 and 106 is subjected to an ultrasonic welding treatment carried out with a sonotrode S.

The welding treatment (the ultrasound welding treatment just mentioned may represent a preferred choice, which however may be substituted with equivalent techniques, for example thermal welding) provides coherence to the previously formed sandwich structure, preventing its delamination (that is, detachment of the layers 102, 104, 106).

In one embodiment, before application of the layer 104 onto the layer 106, two additional lines of spread adhesive material 108' may be applied (represented schematically with broken lines in the figures) having characteristics substantially analogous to those previously described with reference to the lines of spread adhesive 108.

The lines 108' are intended to provide a connecting action between the layer 106 and the layer 104 substantially similar to that provided by the lines 108 between the layer 106 and the layer 102. The welding treatment to which the sandwich material 102, 104, 106 is subjected confers characteristics of "breathability" to the same.

Breathability, as is well known in the field of sanitary products, describes the capability of a laminar material to be permeable to aeriforms (air and vapours) so to allow the skin of the user to "breath".

In one embodiment, such treatment is substantially comparable to the formation of an array of openings or perforations made in the sandwich material by means of suitably shaped protuberances of the welding pattern P. During the welding phase, the elastic material of the sandwich is perforated.

The view in FIG. 7 illustrates the various parts involved in the welding process in a general way and apart from each other for greater clarity. FIG. 8 instead illustrates in greater detail the positioning of the parts indicated by the arrow VIII in FIG. 7 and therefore it represents more realistically the result obtained with the welding/perforating action.

As can be seen in FIG. 8, perforation and welding are performed in a single phase when the molecules of the materials found in correspondence to the patterns P are acted on by the sonotrode or a mechanical welder and the heat generated by molecular friction melts them, causing them to migrate rapidly toward the sides of the pattern P and generating a perforation with a welded edge all around it.

At the end of this treatment, the web 100, having its sandwich structure, formed by the laminar layers 102 and 104 with the extensible layer 106 interposed between them, completed, can be released and, for example, wound onto reels in preparation for its successive use.

Once released from the retention that prevents its retraction, the web 100 assumes the transverse profile visible in FIG. 9, which in fact represents, a side panel 16 viewed in section, formed (in a way, itself known) starting from tape 100 and applied (in a way, itself known as well) to the article 10 in FIG. 1.

With the web 100/panel 16 maintained in the absence of traction efforts, the layer 106 contracts, determining the retraction of the layers 102 and 104 in a transversal wrinkling of the zones comprised between the adhesive lines 108 (and, if present, 108'—it will be appreciated that such lines 108' do not necessarily need to coincide exactly with the lines 108).

Examination of FIG. 7 highlights the fact that the ultrasound welding action (or equivalent) intended to provide coherence to the sandwich structure against delamination, and the corresponding perforating action destined to confer characteristics of breathability to such structure, are obtained without performing said welding and perforating (if performed) operations in correspondence to the connecting adhesive lines 108 (and, when present, 108').

The presence of the strips of spread adhesive 108 (and possibly 108')—which, precisely because they are obtained by spreading, have a certain width, for example, in the order of 4-6 mm, allows the fabrication of a tape 10 with a sandwich structure adapted to be extended transversally with respect to its longitudinal direction of extension to the point of bringing it to a width equal to approximately 200% (that is, three times) its width at rest (as is represented in FIG. 9). All of this without giving rise to phenomena of detachment, weakening or alteration of the material in the web 10; this also concerning any possible risk of separation of the layers 102, 104 and 106 one from the other.

This excellent transverse extensibility behaviour is accompanied by the fact that the material 100 described herein is elastically extensible transversely, starting from the resting condition represented in FIG. 9 up to an extension condition substantially comparable to that represented in FIG. 4, that is, a condition in which the extensible layer 106 is interposed sandwich-like between the two layer 102 and 104 maintained in their original flat condition.

Once extended laterally to the point of reaching such condition, the web 100 has remarkable resistance to any further attempt at transversal extension: this because such further extension would imply the need to extend also the laminar layer 102 and 104, which by their nature are substantially not extensible.

As was stated in the introduction of the description, this behaviour (initial elastic extensibility to a higher extension value, followed by a substantial non extensibility) is advantageous for application in some sanitary articles, for example, for the fabrication of elastic side panels in sanitary articles wearable as pants.

FIG. 10 refers schematically to the possibility of applying the method referred to in FIGS. 2 to 7 to the realisation of an extensible tape material, reproducing the laterally extensible tape or web structure 100 considered herein in a paired (or generally, multiple) form.

In particular, FIG. 10 refers to a solution that envisions the application of four lines of spread adhesive material 108, with two lines 108 located more internally and close to together (for example, at a distance in the order of 1-2 cm).

Once the elastic material 106 is laminated onto the material 102, longitudinal cutting of the elastic material 106 is performed, thus dividing it into two strips of material.

After being cut, the material 104, which, as was previously said, may have strips of glue 108' in correspondence to the strips 108, is laminated. The sandwich structure can then be subjected to the welding and perforation process.

The cutting operation may be performed, for example, by means of a knife rotating around an axis XZ, exploiting the fact that in correspondence to the cutting point, the bottom laminar material 102 tends to automatically form a sort of groove.

This because an annular depression is provided on the anvil or counter roller and the material 102 wedges into this groove, forming a crease that is not affected by the cutting action.

The cutting operation, performed when the layer 106 is still maintained extended transversally, allows the portion of such layer comprised internally between the lines 108 to be cut in half, with the consequent formation of two tails 106' of extensible material that is no longer extended.

The net achievable result is the formation of a tape having a structure substantially similar to that of the web 100 previously described, which can also be cut longitudinally along its midline, so to form two tapes of material 100 substantially identical to the tape material previously seen. The two tapes thus obtained (once again, such tapes could also be more than two in number) can then be wound already separated or yet to be separated and/or can be sent to a utilisation process, proceeding, in the case in which they are not yet separated, to their separation (that is, to the cutting of the sandwich 100 in a position intermediate between the two tapes 106) only in a successive phase of the production process of the single use absorbent product, for example at the time in which the two tapes are separated from each other because they are intended to form elastic side panels located on opposite sides of the same sanitary product.

It is possible to separate the two tapes by performing an intermittent pre-cutting of the web 100 during the sandwich construction operation, which allows separation of the two sheets with a simple pulling action.

It is evident that, to one skilled in the field nothing changes from a technological point of view if the material 100 is produced with the sheet 102 much larger than sheet 104.

The advantage of this type of product is that it provides more economical panels, and, in the case of adult incontinence products, better fitting, that is, the elasticity of the side panels is exploited to provide better fitting, and the rigidity of the material 102 is exploited to guarantee that the product weighed down with the exudates of the wearer does not slide down. In other words, an actual elastic belt is provided.

The above-said product can be improved further using a non-woven fabric with loop characteristics for the tape 102, that is, capable of being engaged by the hooks (that is, the micro hooks) of mechanical closing systems (label) normally used for these products.

Naturally, without prejudice to the underlying principle of the invention, the details of realisation and the embodiments may vary, even appreciably, with reference to what has been described herein by way of non-limiting example only, without departing from the scope of the invention as defined in the annexed claims. This is particularly, but not exclusively valid for the possibility—mentioned previously—of using materials different from those previously referred to by way of example for the purpose of realising the sandwich 102, 104 and 106. For example, one or both of the layers 102, 104 could be constituted by a film of plastic material such as polyethylene instead of the non-woven fabric. As a further example, the elastic material could be polyurethane foam, which, being breathable material itself, would further increase the breathability of the side panels 16.

The invention claimed is:

1. An extensible laminar material comprising:
   an extensible layer configured to be extendable from a non-extended condition to an extended condition, and
   at least one laminar layer, the extensible layer being coupled to the at least one laminar layer by welds arranged in a selected pattern and by lines of spread adhesive applied at selected locations such that the extension of said extensible layer from the non-extended condition to the extended condition causes the extension of said at least one laminar layer and the return of said extensible layer toward said non-extended condition causes the pulling of said at least one laminar layer into a wrinkled condition, wherein said welds are absent in all the selected locations where said extensible layer and said at least one laminar layer are coupled by said lines of spread adhesive.

2. The material according to claim 1, further comprising an array of openings configured to confer aeriform-permeability characteristics to the material, wherein said openings are absent in locations where said extensible layer and said at least one laminar layer are coupled by said lines of spread adhesive.

3. The material according to claim 1, having a sandwich structure with said extensible layer interposed between two of said laminar layers.

4. The material according to claim 3, wherein said lines of spread adhesive are on both sides of said extensible layer causing it to be anchored with respect to both of said laminar layers.

5. The material according to claim 1, wherein said lines of spread adhesive have a width between 2 and 10 mm.

6. The material according to claim 1, wherein said at least one laminar layer is comprised of a material selected from the group consisting of a non-woven fabric and a film of plastic material.

7. The material according to claim 1, wherein said welds comprise ultrasound welds.

8. The material according to claim 1, wherein the material is arranged in the form of a web which is extensible transversally to a longitudinal extension of the web, and wherein said lines of spread adhesive extend along sides of the web.

9. The material according to claim 3, wherein said sandwich structure comprises:
   a base laminar layer with a plurality of pairs of said lines of spread adhesive applied thereto,
   a plurality of said extensible layers anchored to said base laminar layer by means of corresponding pairs of said lines of spread adhesive, and
   at least one additional laminar layer, wherein said extensible layers are interposed between said base laminar layer and said at least one additional laminar layer.

10. The material according to claim 1, configured for the manufacture of sanitary articles.

11. The material according to claim 9, further comprising an array of openings configured to confer aeriform-permeability characteristics to the material, wherein said openings are absent in locations where said extensible layer and said at least one laminar layer are coupled by said lines of spread adhesive.

12. The material according to claim 1, wherein said lines of spread adhesive have a width between 4 and 6 mm.

* * * * *